(12) United States Patent
Otsuka et al.

(10) Patent No.: US 12,098,755 B2
(45) Date of Patent: Sep. 24, 2024

(54) FLEXIBLE MEMBER

(71) Applicant: NHK SPRING CO., LTD., Kanagawa (JP)

(72) Inventors: Motoyuki Otsuka, Kanagawa (JP); Takafumi Hirata, Kanagawa (JP); Shimpei Kurokawa, Kanagawa (JP); Soichi Nakayama, Kanagawa (JP); Masahiro Inaba, Kanagawa (JP)

(73) Assignee: NHK SPRING CO., LTD., Kanagawa (JP)

( * ) Notice: Subject to any disclaimer, the term of this patent is extended or adjusted under 35 U.S.C. 154(b) by 411 days.

(21) Appl. No.: 17/601,425

(22) PCT Filed: Apr. 10, 2020

(86) PCT No.: PCT/JP2020/016214
§ 371 (c)(1),
(2) Date: Oct. 4, 2021

(87) PCT Pub. No.: WO2020/209386
PCT Pub. Date: Oct. 15, 2020

(65) Prior Publication Data
US 2022/0193932 A1      Jun. 23, 2022

(30) Foreign Application Priority Data

Apr. 11, 2019   (JP) .................................. 2019-075948

(51) Int. Cl.
*F16F 1/32*       (2006.01)
*A61B 17/29*      (2006.01)
(Continued)

(52) U.S. Cl.
CPC .............. *F16F 1/328* (2013.01); *A61B 17/29* (2013.01); *A61B 34/71* (2016.02); *F16F 1/025* (2013.01);
(Continued)

(58) Field of Classification Search
CPC ... F16F 1/328; F16F 1/025; F16F 3/02; A61B 34/71; A61B 17/29; A61B 2034/301; A61B 2017/00305; B25J 9/0015; B25J 18/06
See application file for complete search history.

(56) References Cited

U.S. PATENT DOCUMENTS 4,901,987 A * 2/1990 Greenhill .................. F16F 1/06
                                                    267/182
5,072,917 A * 12/1991 Pleva ........................ F16F 1/32
                                                    411/162

(Continued)

FOREIGN PATENT DOCUMENTS

CN      108953440      12/2018
JP      S60172035      11/1985
(Continued)

OTHER PUBLICATIONS

Office Action of China Counterpart Application, with English translation thereof, issued on Jun. 7, 2023, pp. 1-11.
(Continued)

*Primary Examiner* — Thomas W Irvin
(74) *Attorney, Agent, or Firm* — JCIPRNET

(57) ABSTRACT

Provided is a flexible member that can exhibit excellent load resistance and flexibility while achieving a reduction in size. This flexible member includes: a main body part which has multiple wave washers stacked in an axial direction and joined to each other, and the main body part is able to be bent with respect to the axial direction due to elastic deformation of the wave washers; and a linking member that is elastically deformable, the linking member being provided at an end part of the main body part and being linked to other member. A deformation amount of the linking member is smaller than a deformation amount of the wave washer, when the main body part is bent.

4 Claims, 12 Drawing Sheets

(51) Int. Cl.
    *A61B 34/00*         (2016.01)
    *A61B 34/20*         (2016.01)
    *F16F 1/02*          (2006.01)
    *A61B 17/00*         (2006.01)
    *A61B 34/30*         (2016.01)
    *B25J 9/00*          (2006.01)
    *B25J 18/06*         (2006.01)

(52) U.S. Cl.
    CPC ............... *A61B 2017/00305* (2013.01); *A61B 2034/301* (2016.02); *B25J 9/0015* (2013.01); *B25J 18/06* (2013.01)

(56) References Cited

U.S. PATENT DOCUMENTS

| | | | | |
|---|---|---|---|---|
| 5,558,393 | A * | 9/1996 | Hawkins | F16F 1/328 267/164 |
| 6,068,250 | A * | 5/2000 | Hawkins | F16F 1/328 267/164 |
| 6,758,465 | B1 * | 7/2004 | Greenhill | F16F 1/06 267/162 |
| 7,210,181 | B1 * | 5/2007 | Price | A47C 27/065 5/255 |
| 11,576,740 | B2 * | 2/2023 | Kurokawa | A61B 17/29 |
| 2003/0222385 | A1 * | 12/2003 | Cai | F16F 1/328 267/162 |
| 2011/0125166 | A1 | 5/2011 | Cooper et al. | |
| 2013/0312564 | A1 * | 11/2013 | Kim | B25J 18/06 901/21 |
| 2015/0314451 | A1 | 11/2015 | Nixon | |
| 2016/0235274 | A1 * | 8/2016 | Graham | A01K 85/005 |
| 2018/0370045 | A1 * | 12/2018 | Kan | A61B 34/71 |
| 2020/0323600 | A1 * | 10/2020 | Kurokawa | A61B 34/71 |
| 2022/0145956 | A1 * | 5/2022 | Kawai | F16F 1/328 |
| 2022/0193933 | A1 * | 6/2022 | Kurokawa | B25J 18/06 |

FOREIGN PATENT DOCUMENTS

| | | |
|---|---|---|
| JP | S63140908 | 9/1988 |
| JP | H09229119 | 9/1997 |
| JP | 2014038075 | 2/2014 |
| JP | 2019034081 | 3/2019 |
| WO | 2019039362 | 2/2019 |
| WO | 2019073860 | 4/2019 |

OTHER PUBLICATIONS

"International Search Report (Form PCT/ISA/210) of PCT/JP2020/016214", mailed on Jul. 7, 2020, with English translation thereof, pp. 1-5.
"Search Report of Europe Counterpart Application", issued on May 16, 2022, pp. 1-8.
Office Action of China Counterpart Application, with English translation thereof, issued on Nov. 1, 2023, pp. 1-9.
"Decision on Rejection of China Counterpart Application", issued on Feb. 29, 2024, with English translation thereof, p. 1-p. 11.

* cited by examiner

FLEXIBLE MEMBER

CROSS-REFERENCE TO RELATED APPLICATION

This application is a 371 application of the international PCT application serial no. PCT/JP2020/016214, filed on Apr. 10, 2020, which claims the priority benefit of Japan application no. 2019-075948, filed on Apr. 11, 2019. The entirety of each of the above-mentioned patent applications is hereby incorporated by reference herein and made a part of this specification.

TECHNICAL FIELD

The present invention relates to a flexible member provided for a joint functioning part of a robot or the like.

BACKGROUND ART

Some robots, manipulators, actuators, and the like in various fields have a joint functioning part capable of performing bending operation using a flexible member. Regarding a flexible member used in such a joint functioning part, Japanese Patent Laid-Open No. 2014-38075 discloses a coil spring.

A coil spring can secure a high degree of freedom with respect to bending operation of a joint functioning part. However, there has been a limit to reduction in size of a coil spring due to the need to secure load resistance and flexibility.

SUMMARY OF INVENTION

Technical Problem

A problem to be solved is that there is a limit in securing load resistance and flexibility while achieving reduction in size.

Solution to Problem

The present invention provides a flexible member which can have excellent load resistance and flexibility while achieving reduction in size. This flexible member includes: a main body part that has a plurality of wave washers stacked in an axial direction and joined to each other, and the main body part is able to be bent with respect to the axial direction due to elastic deformation of the wave washers; and a linking member that is elastically deformable, the linking member being provided at an end part of the main body part and being linked to other member. A deformation amount of the linking member is smaller than a deformation amount of the wave washer, when the main body part is bent.

Advantageous Effects of Invention

According to the present invention, the main body part of the flexible member can be bent due to deformation of the plurality of wave washers. Therefore, it is possible to obtain a flexible member having excellent load resistance and flexibility while achieving reduction in size.

Furthermore, in the present invention, since the linking members are deformed when the main body part is bent, a stress acting on the wave washers at the end parts of the main body part can be alleviated. As a result, the present invention can improve durability of a flexible member.

DESCRIPTION OF EMBODIMENT

An objective of obtaining a flexible member which can have excellent load resistance and flexibility while achieving reduction in size is realized while durability is improved.

That is, the flexible member includes: a main body part that has a plurality of wave washers stacked in an axial direction and joined to each other, and the main body part is able to be bent with respect to the axial direction due to elastic deformation of the wave washers; and a linking member that is elastically deformable, the linking member being provided at an end part of the main body part and being linked to other member. The linking member has a constitution in which a deformation amount of the linking member is smaller than a deformation amount of the wave washer, when the main body part is bent.

Various elastic members can be employed as the linking member. However, an annular plate member having larger spring constant than that of the wave washer of the main body part may be adopted.

In this case, the linking member may include: a plurality of flat washers stacked in the axial direction and joined to each other.

The plurality of wave washers may individually include a plurality of mountain parts and valley parts individually provided between the mountain parts in a circumferential direction and be joined in a state in which the mountain parts and the valley parts of adjacent wave washers abut each other. A plurality of adjacent flat washers may be joined to each other at positions corresponding to joint portions of the wave washers.

Example 1

Structure of Manipulator

Figure 1:
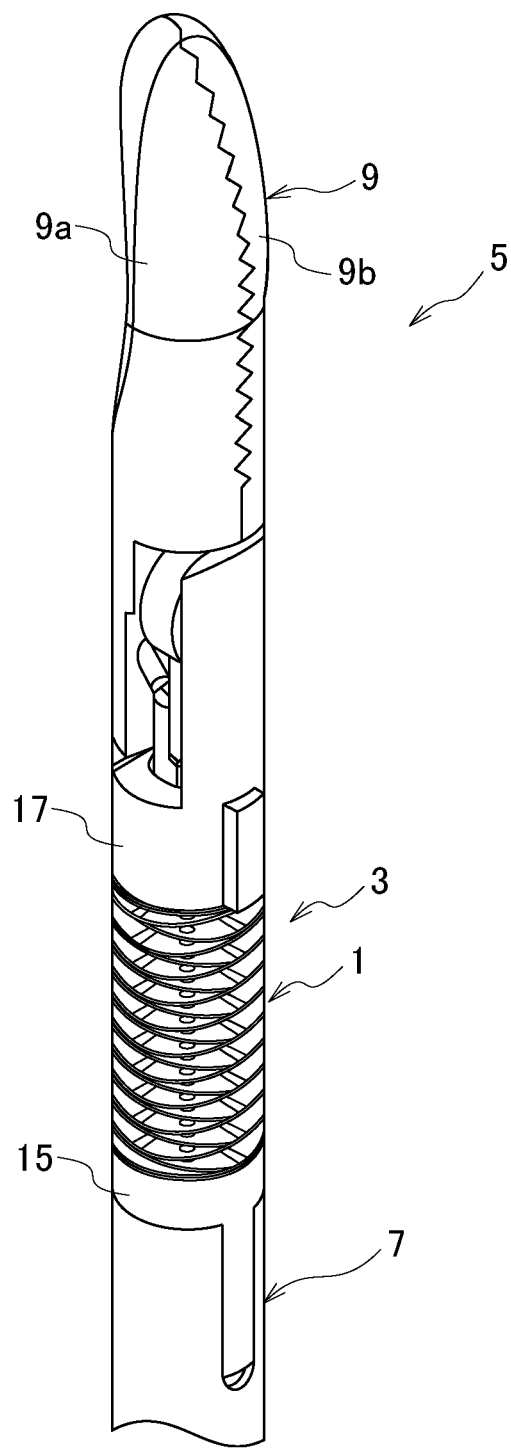
FIG. 1 is a perspective view illustrating a manipulator using a flexible member according to an Example 1 of the present invention.
Figure 2:
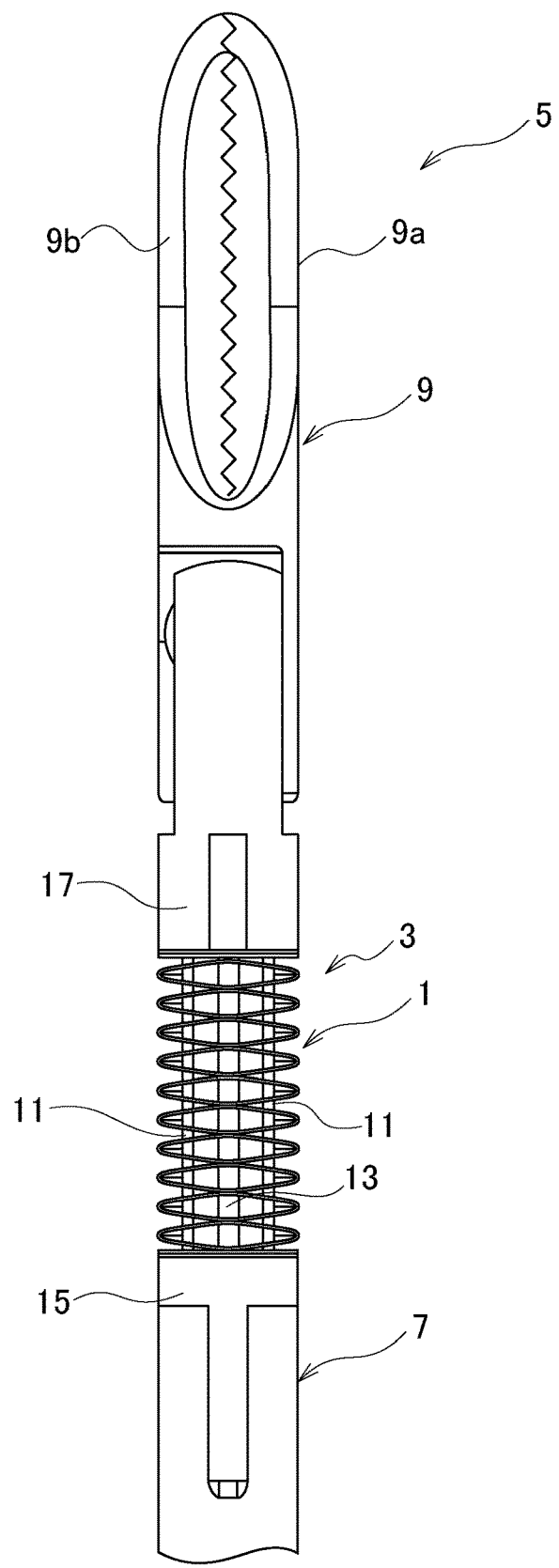
FIG. 2 is a front view illustrating the manipulator in FIG. 1.
Figure 3:
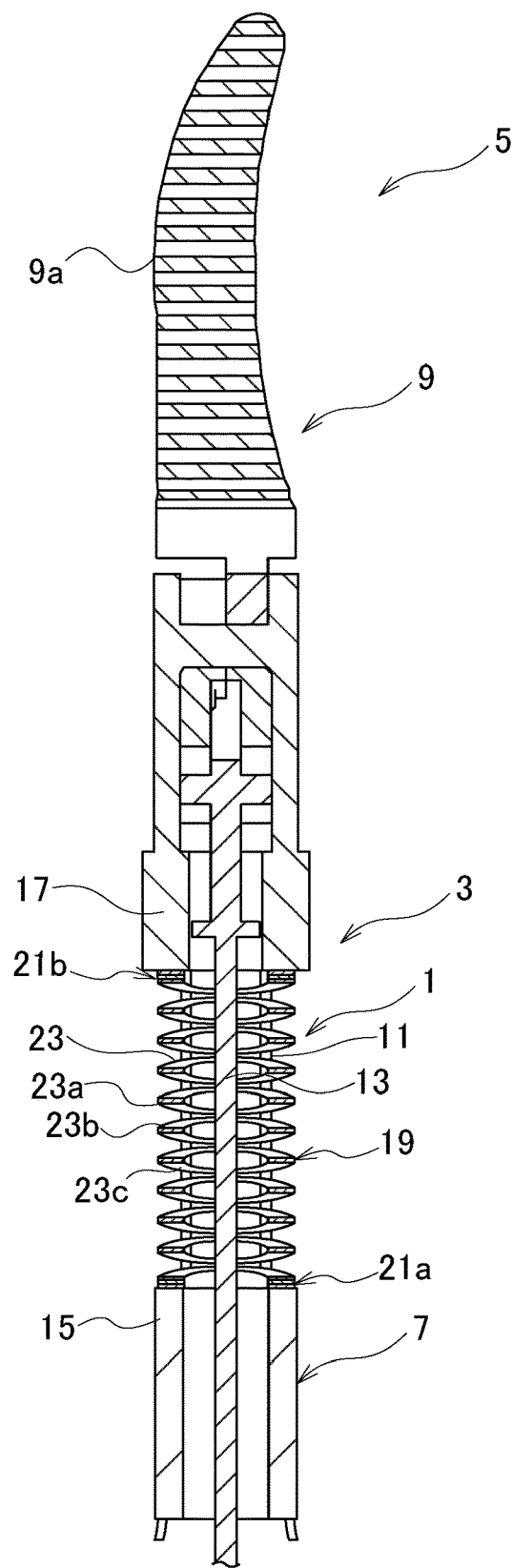
FIG. 3 is a cross-sectional view of the manipulator in FIG. 1.

FIG. 1 is a perspective view illustrating a manipulator using a flexible member according to an Example 1 of the present invention, FIG. 2 is a front view of the same, and FIG. 3 is a cross-sectional view of the same.

The present example will be described regarding a medical manipulator 5 as an example of a robot, a manipulator, or an actuator which has a joint functioning part 3 using a flexible member 1.

The manipulator 5 constitutes a tip of a robot arm of a surgical robot and is operated by a doctor or the like. The manipulator 5 may be a manual manipulator which is directly operated by a doctor or the like without being attached to a surgical robot. In addition, a robot, a manipulator, or an actuator in which the flexible member 1 can be applied is not limited to the manipulator 5, and the flexible member 1 may be adopted in other fields such as industrial robots.

The manipulator 5 includes a shaft part 7, the joint functioning part 3, and an end effector 9.

The shaft part 7 is formed to have a hollow tubular shape, for example, a cylindrical shape. Driving wires 11 for driving the joint functioning part 3 or a push-pull cable 13 for driving the end effector 9 passes through the inside of the shaft part 7. The end effector 9 is provided at a tip of the shaft part 7 with the joint functioning part 3 therebetween.

The joint functioning part 3 performs bending operation with respect to an axial direction in response to an operation of the driving wires 11. The axial direction denotes a direction along an axial center of the flexible member 1, which will be described below. However, there is no need for the axial direction to be a direction strictly parallel to the axial center. Therefore, the axial direction also includes a direction slightly inclined with respect to the axial center. Details of the joint functioning part 3 will be described below.

The end effector 9 is an instrument which is attached to a movable part 17 of the joint functioning part 3 and performs operation according to a purpose. The end effector 9 of the present example is a forceps and includes a pair of clasping parts 9a and 9b. This end effector 9 can be directed in a desired direction in response to bending operation of the joint functioning part 3. In addition, the pair of clasping parts 9a and 9b can be opened and closed in response to an operation of the push-pull cable 13.

The end effector 9 is not limited to a forceps, for example, it can be scissors, a clasping retractor, a needle driver, a camera, or the like.

Structure of Joint Functioning Part

Figure 4:
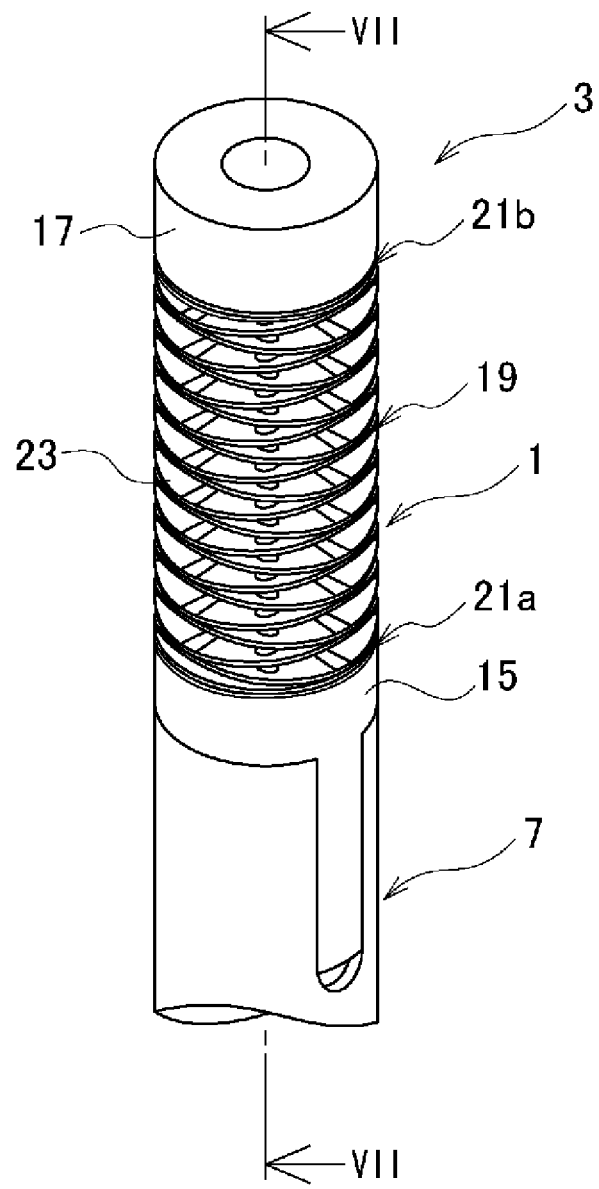
FIG. 4 is a perspective view mainly illustrating a joint functioning part in which a part of the manipulator in FIG. 1 is omitted.
Figure 5:
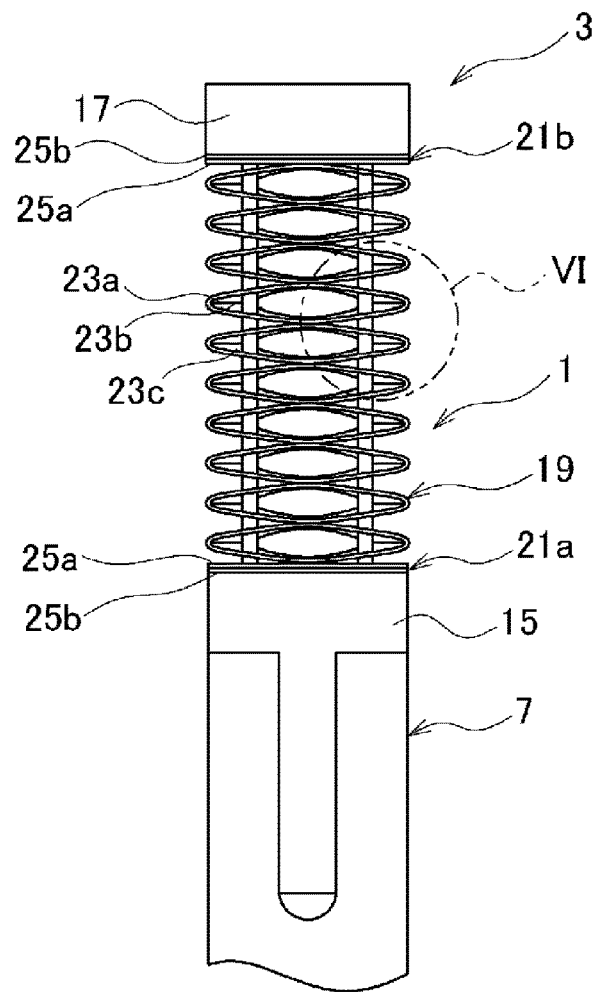
FIG. 5 is a side view mainly illustrating the joint functioning part in FIG. 4.
Figure 6:
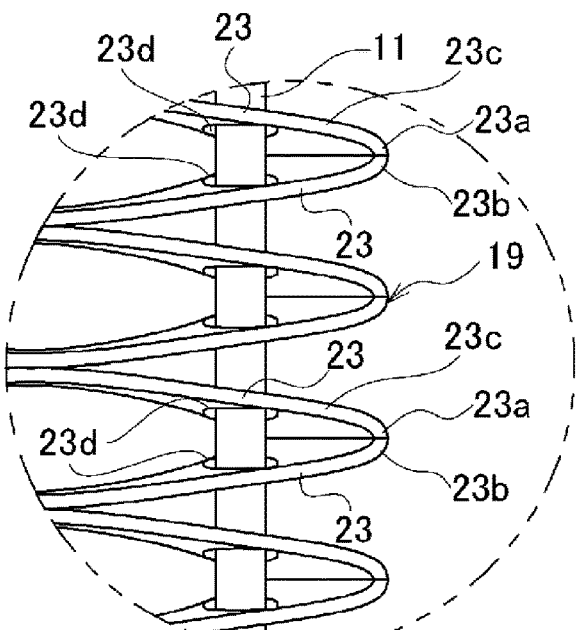
FIG. 6 is an enlarged view of the VI part in FIG. 5.
Figure 7:
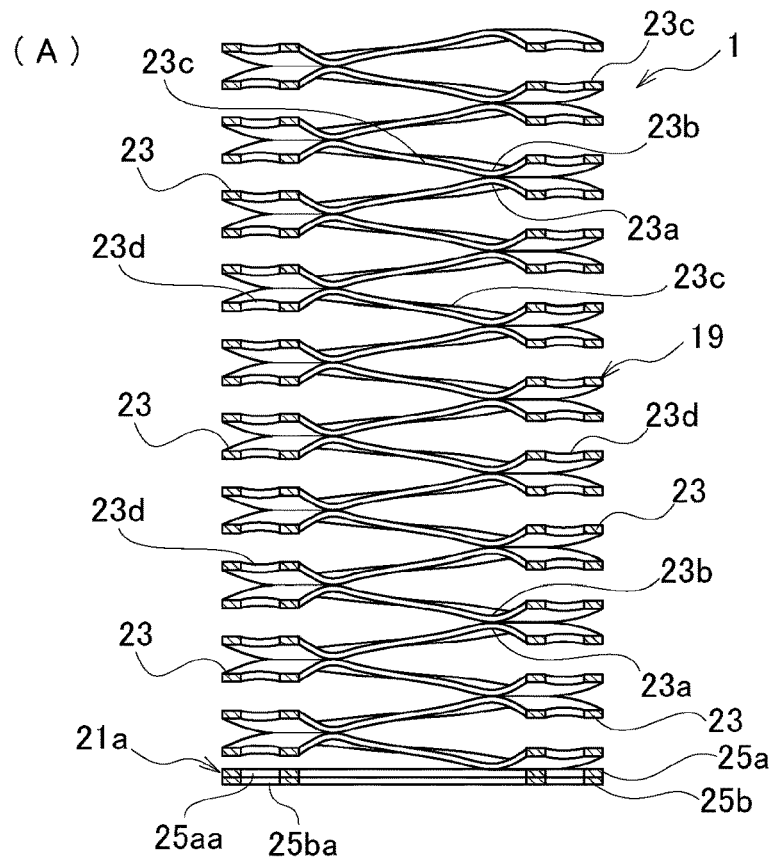
In FIGS. 7, (A) and (B) are cross-sectional views illustrating a flexible member of the joint functioning part along line VII-VII in FIG. 4, in which (A) of FIG. 7 illustrates the flexible member at a normal time, and (B) of FIG. 7 illustrates the flexible member at the time of being bent.
Figure 7:
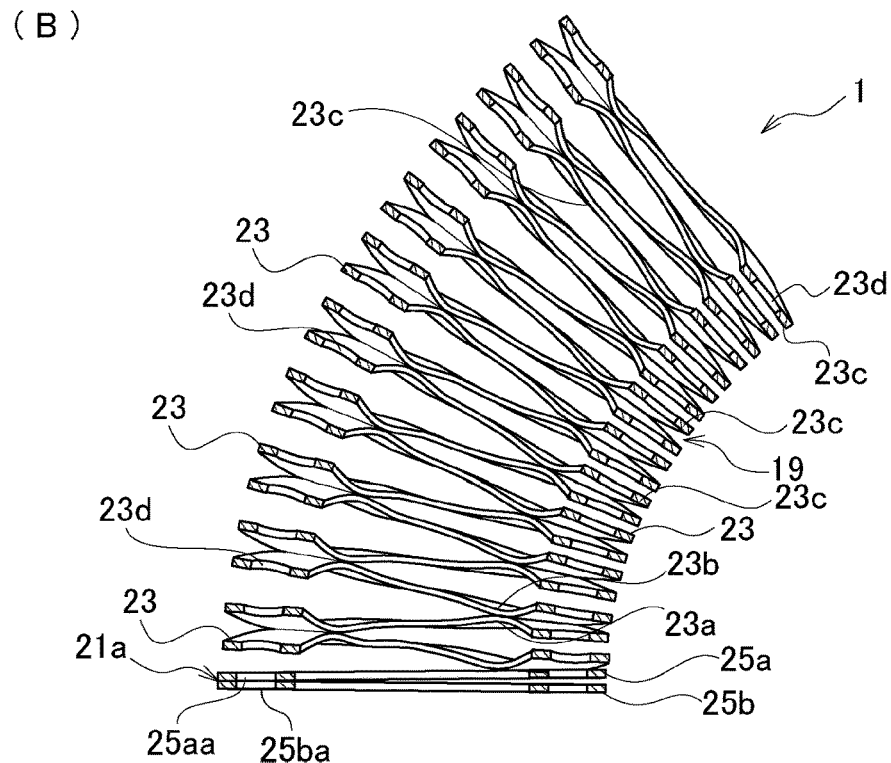
Figure 8:
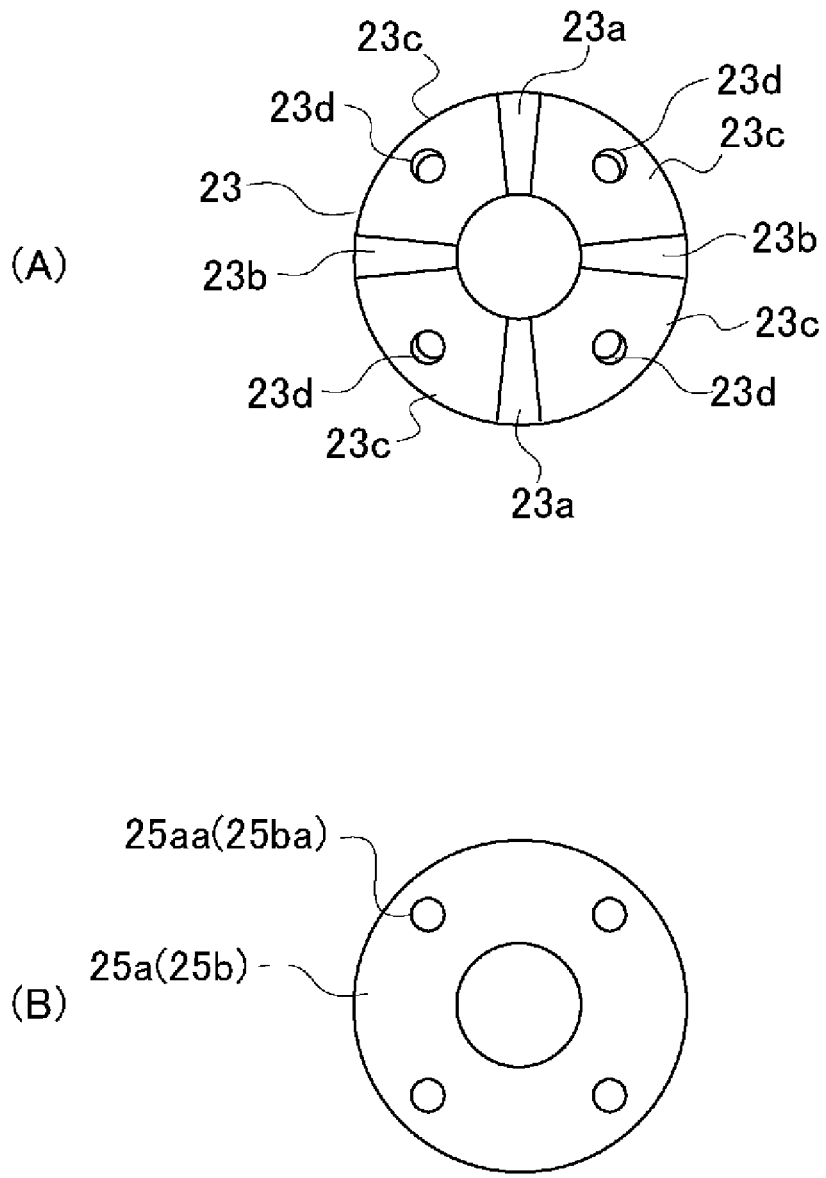
In FIG. 8, (A) is a plan view illustrating a wave washer used in a main body part of the flexible member, and (B) is a plan view illustrating a flat washer used in a linking part of the flexible member.

FIG. 4 is a perspective view mainly illustrating the joint functioning part 3 in which a part of the manipulator 5 in FIG. 1 is omitted, FIG. 5 is a side view of the same, and FIG. 6 is an enlarged view of the VI part in FIG. 5. In FIGS. 7, (A) and (B) are cross-sectional views illustrating the flexible member 1 of the joint functioning part 3 along line VII-VII in FIG. 4, in which (A) of FIG. 7 illustrates the flexible member 1 at a normal time, and (B) of FIG. 7 illustrates the flexible member 1 at the time of being bent. In FIG. 8, (A) is a plan view illustrating a wave washer used in a main body part of the flexible member, and (B) is a plan view illustrating a flat washer used in a linking part of the flexible member.

As in FIG. 1 to (B) of FIG. 8, the joint functioning part 3 includes a base part 15, the movable part 17, and the flexible member 1.

The base part 15 is formed of a metal or the like to have a columnar shape and is attached to the tip of the shaft part 7. The push-pull cable 13 is inserted through an axial center part of the base part 15 in the axial direction. Around the push-pull cable 13, the driving wires 11 are inserted through the base part 15 in the axial direction.

The movable part 17 is formed of a metal or the like to have a columnar shape and is attached to the end effector 9. An axial center part of the movable part 17 is inserted through the push-pull cable 13. A tip of the push-pull cable 13 is linked to the end effector 9.

This movable part 17 is supported by the base part 15 with the flexible member 1 therebetween. Tip parts of the driving wires 11 are fixed to the movable part 17. For this reason, the movable part 17 is deformed with respect to the base part 15 due to an operation of the driving wires 11 and can direct the end effector 9 in a desired direction.

The flexible member 1 enables the joint functioning part 3 to perform bending operation. The flexible member 1 is interposed between the base part 15 and the movable part 17. The flexible member 1 is bent in response to deformation of the movable part 17 with respect to the base part 15. The driving wires 11 and the push-pull cable 13 pass through the flexible member 1 in the axial direction.

The flexible member 1 includes: a main body part 19; and linking members 21a and 21b.

The main body part 19 has a plurality of wave washers 23. The wave washers 23 are stacked in the axial direction, and wave washers 23 adjacent to each other in the axial direction are joined to each other. The main body part 19 can be bent due to elastic deformation of the wave washers 23.

Each of the wave washers 23 is a plate member formed of a metal or the like to have a closed ring shape. The wave washers 23 of the present example are plate members formed of stainless steels to have toric shapes. A width of the wave washer 23 between inner and outer circumferences in a radial direction and a plate thickness thereof are uniform in a circumferential direction. However, the widths and the plate thicknesses of the wave washers 23 may not be uniform in the circumferential direction.

Each of the wave washers 23 has a plurality of mountain parts 23a and valley parts 23b in the circumferential direction. Each of the valley parts 23b is provided between mountain parts 23a adjacent to each other in the circumferential direction. Each of the wave washers 23 of the present example has two mountain parts 23a facing each other in the radial direction and has two valley parts 23b facing each other in the radial direction between the mountain parts 23a. Therefore, in the present example, the mountain parts 23a and the valley parts 23b are alternately provided at intervals of 90 degrees in the circumferential direction.

The mountain parts 23*a* and the valley parts 23*b* lie from the inner circumference to the outer circumference of the wave washer 23 in the radial direction. The mountain parts 23*a* and the valley parts 23*b* are formed to be curved in arc shapes in a direction opposite to the axial direction. In wave washers 23 adjacent to each other in the axial direction, the mountain parts 23*a* of the wave washer 23 on one side abut the valley parts 23*b* of the wave washer on the other side. Due to expansion and contraction of the mountain parts 23*a* and the valley parts 23*b*, each of the wave washers 23 can be deformed due to elastic expansion and contraction in the axial direction.

The mountain parts 23*a* and the valley parts 23*b* abutting each other are joined to each other by a suitable means such as welding or bonding. Accordingly, the stacked state of the main body part 19 of the flexible member 1 is retained.

The mountain parts 23*a* and the valley parts 23*b* may not abut each other. For example, the mountain parts 23*a* and the valley parts 23*b* may have a form in which they slightly deviate from each other in the circumferential direction and abut inclined parts 23*c*.

In each of the wave washers 23, the mountain parts 23*a* and the valley parts 23*b* are connected to each other through the inclined parts 23*c*. The inclined parts 23*c* are inclined in the circumferential direction and have slightly twisted shapes between the inner circumference and the outer circumference.

Insertion holes 23*d* serving as through parts through which the driving wires 11 pass are provided in the inclined parts 23*c*. As a result, a plurality of insertion holes 23*d* is provided in the circumferential direction of the main body part 19. In the present example, four driving wires 11 are individually provided at intervals of 90 degrees in the circumferential direction. Therefore, in accordance with this, four insertion holes 23*d* are individually provided at intervals of 90 degrees in the circumferential direction in each of the wave washers 23.

The insertion holes 23*d* communicate with each other in the axial direction between the inclined parts 23*c* of wave washers 23 adjacent to each other in the axial direction. The driving wires 11 are inserted through the insertion holes 23*d* communicating with each other. Due to this insertion, the flexible member 1 functions as a through part through which the driving wires 11 pass in the axial direction and as a guide retaining the driving wires 11 at a predetermined position.

The insertion holes 23*d* have substantially circular shapes and have diameters larger than the diameters of the driving wires 11. The difference between the diameters allows inclination and deformation of the inclined parts 23*c*. The shapes of the insertion holes 23*d* are not limited to circular shapes and may have different shapes such as rectangular shapes.

The shapes, the materials, and the like of the wave washers 23 can be suitably changed in accordance with characteristics or the like required for the flexible member 1. The number and the radii of curvature of the mountain parts 23*a* and the valley parts 23*b*, the inclination angles of the inclined parts 23*c*, and the like can also be suitably changed in accordance with characteristics or the like required for the flexible member 1.

Both end parts of the main body part 19 are joined to the base part 15 and the movable part 17 respectively with the linking members 21*a* and 21*b* therebetween.

That is, the linking members 21*a* and 21*b* are provided at both end parts of the main body part 19. The linking members 21*a* and 21*b* are elastically deformable members linked to the base part 15 and the movable part 17 (other members). The linking members 21*a* and 21*b* are provided at both end parts of the main body part 19, respectively. However, only the linking member 21*a* at one end part or the linking member 21*b* at the other end part of the main body part 19 may be provided.

The linking members 21*a* and 21*b* of the present example have the same constitutions. Therefore, basically, only the linking member 21*a* on one side will be described. For this reason, FIG. 7 illustrates only the linking member 21*a*.

The linking member 21*a* includes: a plurality of annular plate members having deformation amounts smaller than deformation amounts of (having larger spring constants than) the wave washers 23 of the main body part 19. The linking member 21*a* of the present example includes a pair of flat washers 25*a* and 25*b*. The flat washers 25*a* and 25*b* are stacked each other in the axial direction and are joined to each other. The linking member 21*a* can also be formed using three or more flat washers or other elastic members. In addition, the linking member 21*a* may be constituted by annularly disposing a plurality of members, in place of annular plate members.

The flat washers 25*a* and 25*b* are formed of the same materials as the wave washers 23, have the same inner and outer circumferential diameters and plate thicknesses, and are formed to be flat. Therefore, the flat washers 25*a* and 25*b* are deformed together with the wave washers 23 such that both the flat washers 25*a* and 25*b* are separated when the main body part 19 is bent. However, the deformation amounts of the flat washers 25*a* and 25*b* at this time are smaller than the deformation amounts of the wave washers 23. That is, the linking member 21*a* is constituted such that the deformation amount when the main body part 19 is bent is smaller than the deformation amounts of the wave washers 23. The flat washers 25*a* and 25*b* may be formed using materials different from those of the wave washers 23.

Insertion holes 25*aa* and 25*ba* corresponding to the insertion holes 23*d* of the wave washers 23 are provided in the flat washers 25*a* and 25*b*. The shapes of the insertion holes 25*aa* and 25*ba* are constituted in a manner similar to those of the insertion holes 23*d* of the wave washers 23 and have substantially circular shapes having diameters larger than the diameters of the driving wires 11.

These insertion holes 25*aa* and 25*ba* communicate with the insertion holes 23*d* of the wave washers 23 in the axial direction and allow the driving wires 11 to be inserted therethrough. Therefore, the insertion holes 25*aa* and 25*ba* function as through parts together with the insertion holes 23*d*.

The flat washers 25*a* and 25*b* of the present example are joined to each other at positions corresponding to joint portions of the wave washers 23 of the main body part 19. Therefore, the linking member 21*a* can be smoothly deformed in a manner similar to that of the main body part 19.

Specifically, the flat washer 25*a* on one side abuts the valley parts 23*b* of the wave washer 23 in the axial direction at one end part of the main body part 19 (at the other end part of the linking member 21*b* on the other side) and is joined thereto by means of welding or the like.

The flat washer 25*a* on one side and the flat washer 25*b* on the other side are joined to each other by means of welding or the like at a position in the circumferential direction corresponding to the mountain parts 23*a* of the wave washer 23 at one end part.

The flat washer 25*b* on the other side abuts the base part 15 of the joint functioning part 3 (the movable part 17 in the linking member 21*b* on the other side) and is joined thereto by means of welding or the like at a position in the circumferential direction corresponding to the valley parts 23b of the wave washer 23 at one end part.

Bending Operation of Joint Functioning Part

In the joint functioning part 3, when a doctor operates the manipulator 5, the flexible member 1 is bent by pulling any one of the driving wires 11. This joint functioning part 3 can be bent in all directions through 360 degrees by pulling some driving wires 11 in combination.

When bending is performed by pulling at least any one of the driving wires 11, in the flexible member 1, as in (B) of FIG. 7, the mountain parts 23a and the valley parts 23b are compressed at bending inner side portions with respect to a neutral axis and the mountain parts 23a and the valley parts 23b are extended at bending outer side portions with respect to the neutral axis.

Due to such deformation, the inclined parts 23c through which the operated driving wires 11 are inserted approach each other, and the flexible member 1 in its entirety is bent. Accordingly, the present example realizes bending operation having highly linear load characteristics of a bending angle and a load.

At this time, in the present example, the linking members 21a and 21b at both end parts of the flexible member 1 are deformed such that the flat washers 25a and 25b are separated between the main body part 19 of the flexible member 1 and the base part 15 and between the main body part 19 thereof and the movable part 17.

For this reason, the deformation amounts of the wave washers 23 positioned at both end parts of the main body part 19 of the flexible member 1 are reduced compared to when the wave washers 23 are directly joined to the base part 15 and the movable part 17. Therefore, the linking members 21a and 21b can alleviate stresses acting on the wave washers 23 at both end parts of the main body part 19 of the flexible member 1, and thus durability of the flexible member 1 can be improved.

In addition, since the deformation amounts of the linking members 21a and 21b are smaller than the deformation amount of the main body part 19, the linking members 21a and 21b reliably support both end parts of the main body part 19 with respect to the base part 15 and the movable part 17. Therefore, the linking members 21a and 21b allow the main body part 19 to reliably perform bending and curb fatigue fracture caused by repetitive bending of the main body part 19.

Effects of Example 1

As described above, the flexible member 1 of the present example includes the main body part 19 that has a plurality of wave washers 23 stacked in the axial direction and joined to each other and is able to be bent with respect to the axial direction due to elastic deformation of the wave washers 23, and elastically deformable linking members 21a and 21b that are provided at end parts of this main body part 19 and are linked to the base part 15 and the movable part 17 (other members); and has a constitution in which the deformation amount of the linking member 21a is smaller than the deformation amounts of the wave washers 23 when the main body part 19 is bent.

Therefore, in the present example, the linearity of load characteristics of a bending angle and a load can be enhanced, and it is possible to obtain the flexible member 1 having excellent load resistance and flexibility while achieving reduction in size.

Furthermore, in the present example, since the linking members 21a and 21b are deformed between the main body part 19 of the flexible member 1 and the base part 15 and between the main body part 19 thereof and the movable part 17 when the main body part 19 is bent, stresses acting on the wave washers 23 at both end parts of the main body part 19 of the flexible member 1 can be alleviated. As a result, in the present example, durability of the flexible member 1 can be improved.

In addition, since the linking members 21a and 21b have deformation amounts smaller than the deformation amount of the main body part 19, both end parts of the main body part 19 can be reliably supported with respect to the base part 15 and the movable part 17. Therefore, in the present example, bending of the main body part 19 can be reliably performed, and fatigue fracture caused by repetitive bending of the main body part 19 can be curbed.

The linking members 21a and 21b are annular plate members having larger spring constants than the wave washers 23 of the main body part 19. Therefore, the deformation amounts can be reliably smaller than that of the main body part 19.

Since the linking members 21a and 21b are constituted of a plurality of flat washers 25a and 25b stacked in the axial direction and joined to each other, deformation amounts smaller than that of the main body part 19 can be easily realized.

The plurality of wave washers 23 individually includes a plurality of mountain parts 23a and valley parts 23b between these mountain parts 23a in the circumferential direction. The mountain parts 23a and the valley parts 23b of adjacent wave washers 23 are joined to each other in an abutting state. On the other hand, a plurality of adjacent flat washers 25a and 25b are joined to each other at positions corresponding to the joint portions of the wave washers 23.

Therefore, the linking member 21a can be smoothly deformed together with the main body part 19 in a manner similar to that of the main body part 19.

In addition, in the present example, bending operation can be reliably performed due to expansion and contraction of the mountain parts 23a and the valley parts 23b of the main body part 19.

Moreover, in the present example, since the mountain parts 23a and the valley parts 23b abutting each other are joined to each other, it is possible to obtain the flexible member 1 having an excellent torsional rigidity.

In addition, in the present example, since the plurality of wave washers 23 has the insertion holes 23d through which the driving wires 11 are inserted, the main body part 19 can be utilized as a guide for the driving wires 11 so that the driving wires 11 can be retained at appropriate positions, and thus more stable and accurate bending operation can be performed.

Example 2

Figure 9:
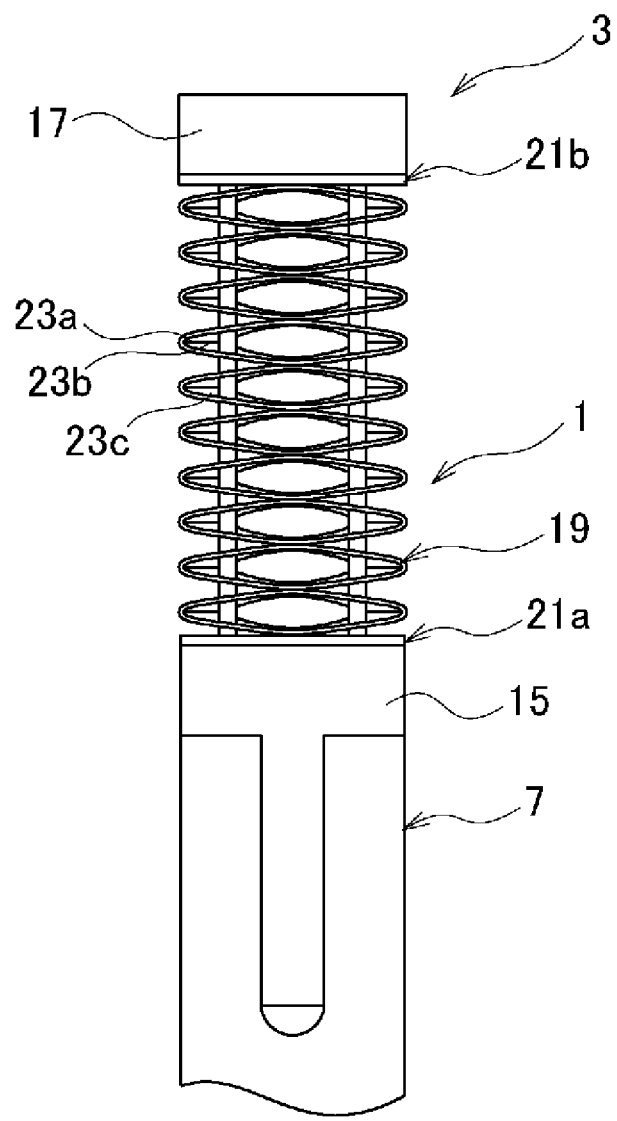
FIG. 9 is a side view mainly illustrating a joint functioning part in which a part of a manipulator using a flexible member according to an Example 2 of the present invention is omitted.

FIG. 9 is a side view mainly illustrating a joint functioning part in which a part of a manipulator using a flexible member according to an Example 2 of the present invention is omitted. In the Example 2, constitutions corresponding to those in the Example 1 are indicated by the same reference signs, and duplicate description will be omitted.

In the present example, each of the linking members 21a and 21b of the flexible member 1 of the joint functioning part 3 is constituted of one flat resin washer such as an elastomer. The linking members 21a and 21b are set to have smaller deformation amounts than the main body part 19 through setting of materials, cross-sectional shapes, or the like. The constitutions are otherwise the same as the constitutions of the Example 1.

The linking members 21a and 21b may be elastic adhesive layers in place of flat resin washers such as elastomers.

According to the Example 2 as well, it is possible to exhibit operational effects similar to those in the Example 1.

Example 3

Figure 10:
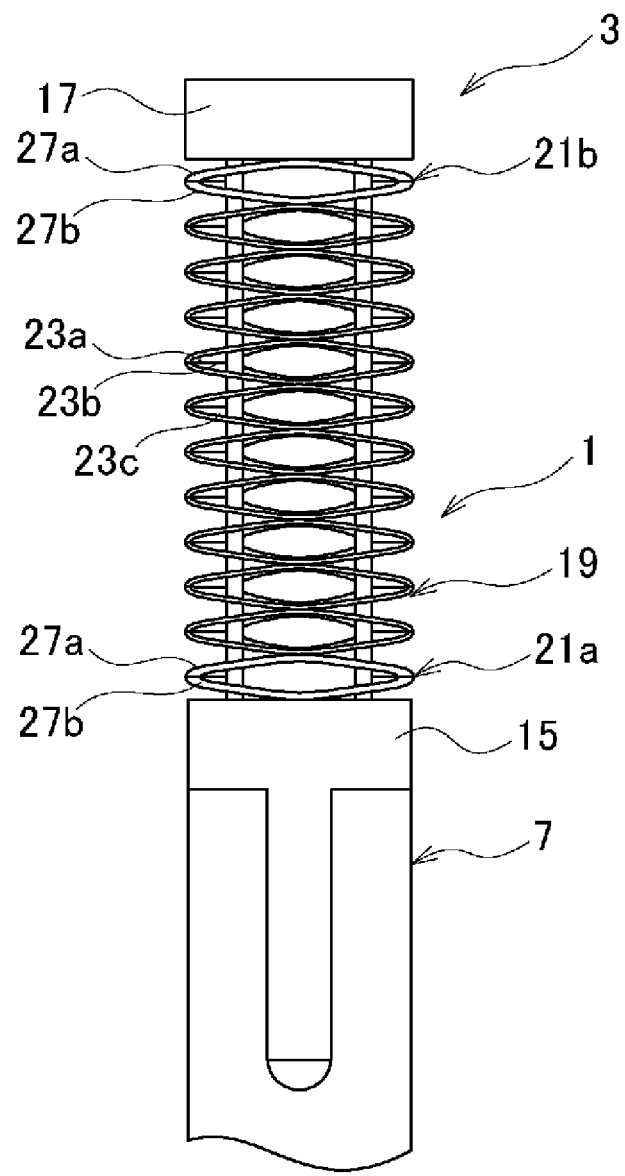
FIG. 10 is a side view mainly illustrating a joint functioning part in which a part of a manipulator using a flexible member according to an Example 3 of the present invention is omitted.

FIG. 10 is a side view mainly illustrating a joint functioning part in which a part of a manipulator using a flexible member according to an Example 3 of the present invention is omitted. In the Example 3, constitutions corresponding to those in the Example 1 are indicated by the same reference signs, and duplicate description will be omitted.

In the present example, the linking members 21a and 21b of the flexible member 1 of the joint functioning part 3 are constituted of wave washers 27a and 27b. These wave washers 27a and 27b are formed to have larger plate thicknesses than the wave washers 23 of the main body part 19, and the deformation amounts thereof are curbed. The constitutions are otherwise the same as the constitutions of the Example 1.

The linking members 21a and 21b can be constituted of materials having larger coefficients of elasticity while having the same plate thicknesses as the wave washers 23 of the main body part 19 or can be wave washers having small wave amounts.

According to the Example 3 as well, it is possible to exhibit operational effects similar to those in the Example 1.

Example 4

Figure 11:
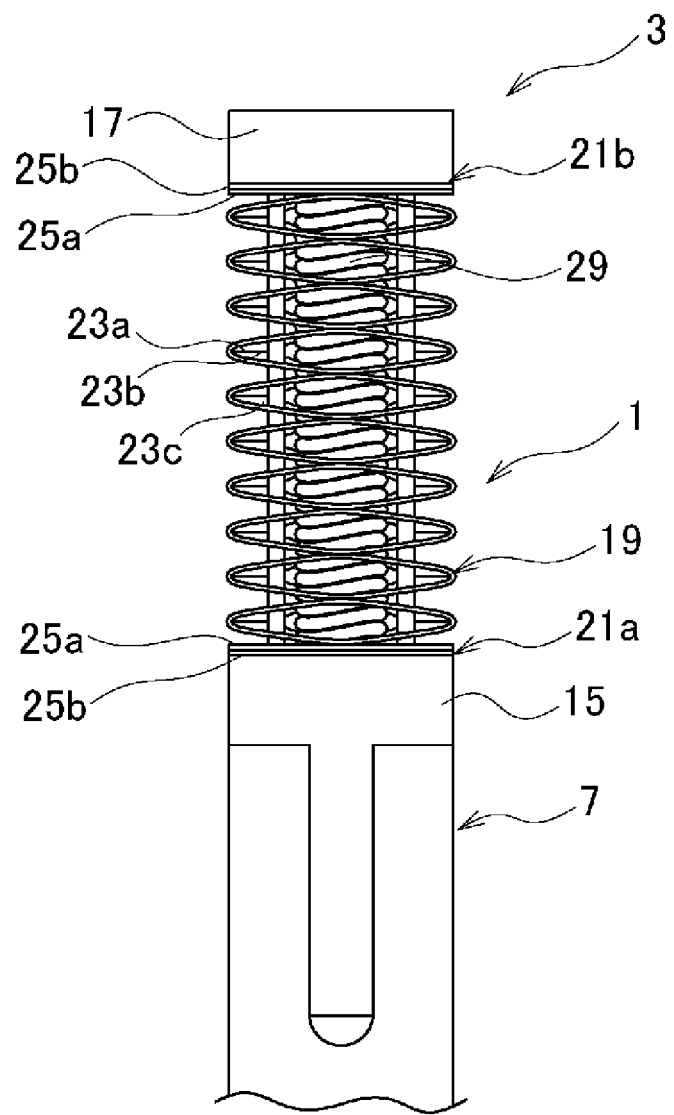
FIG. 11 is a side view mainly illustrating a joint functioning part in which a part of a manipulator using a flexible member according to an Example 4 of the present invention is omitted.

FIG. 11 is a side view mainly illustrating a joint functioning part in which a part of a manipulator using a flexible member according to an Example 4 of the present invention is omitted. In the Example 4, constitutions corresponding to those in the Example 1 are indicated by the same reference signs, and duplicate description will be omitted.

In the present example, elastic members 29 are disposed at the axial center parts of the flexible member 1 of the joint functioning part 3. The constitutions are otherwise the same as the constitutions of the Example 1.

The elastic members 29 are metal coil springs, particularly contact coil springs. Contact coil springs denote coil springs in which coils are in tight contact with each other in a free state. Regarding the elastic members 29, non-contact coil springs having a gap between coils in a free state can be used.

In the elastic members 29 of the present example, a cross section of an element wire of the coil spring has a circular shape. However, a cross section of an element wire of the coil spring can also have a different shape such as a rectangular shape or an elliptical shape.

In the elastic members 29, the push-pull cable 13 is inserted through the inner circumferential side, and the outer circumference is disposed with a gap with respect to the inner circumference of the flexible member 1.

In the axial direction, the elastic members 29 extend throughout at least the entire region of the flexible member 1 and have rigidity with respect to compression set to be higher than that of the flexible member 1. Accordingly, the elastic members 29 can curb careless compression of the flexible member 1 in the axial direction.

In addition, the elastic members 29 can be bent in accordance with the flexible member 1 and has a function of adjusting load characteristics of the flexible member 1 in accordance with load characteristics in a bending direction.

In the Example 4 as well, it is possible to exhibit operational effects similar to those in the Example 1.

Example 5

Figure 12:
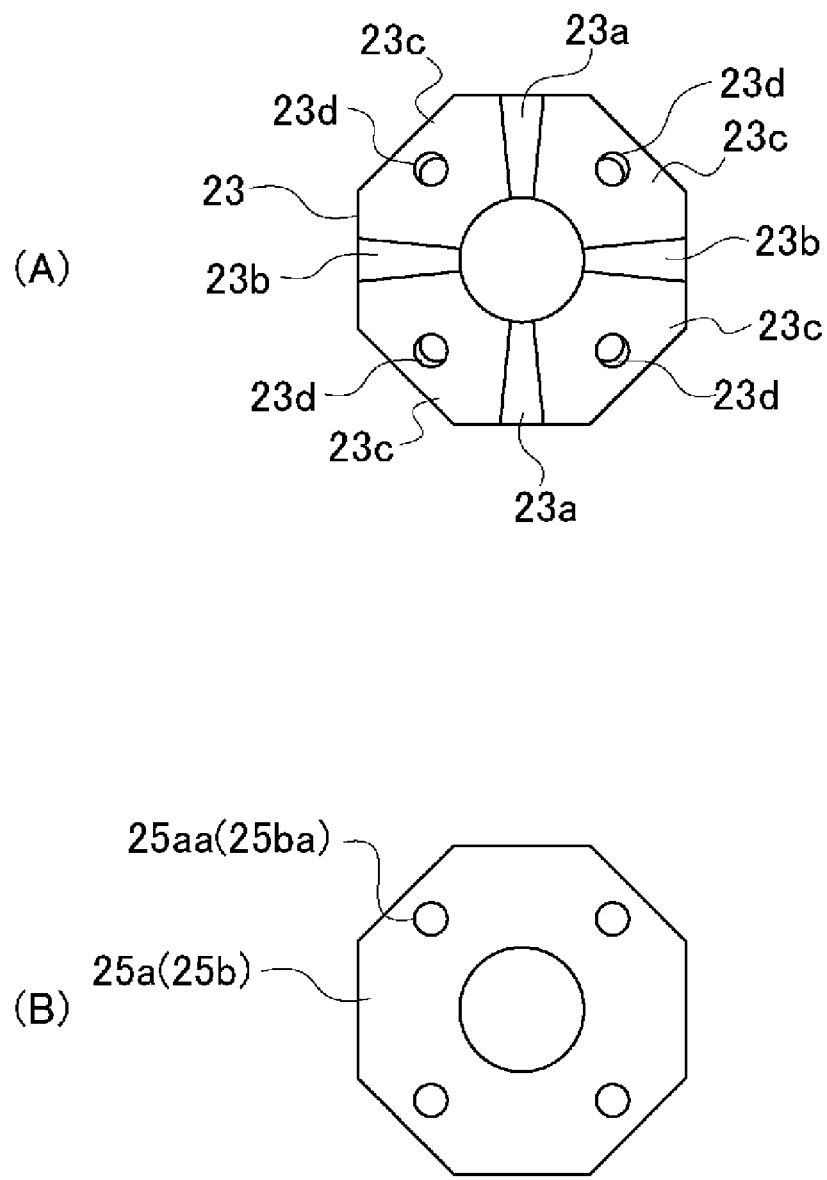
In FIG. 12, (A) is a plan view illustrating a wave washer used in a main body part of a flexible member according to an Example 5 of the present invention, and (B) is a plan view illustrating a flat washer used in a linking part of the flexible member.

In FIG. 12, (A) is a plan view illustrating a wave washer used in a main body part of a flexible member according to an Example 5 of the present invention, and (B) is a plan view illustrating a flat washer used in a linking part. In the Example 5, constitutions corresponding to those in the Example 1 are indicated by the same reference signs, and duplicate description will be omitted.

In the present example, flat surface shapes of the wave washers 23 of the main body part 19 of the flexible member 1 and flat surface shapes of the flat washers 25a and 25b of the linking member 21a are changed compared to those in the Example 1. The constitutions are otherwise the same as the constitutions and the shapes in the Example 1.

In each of the wave washers 23 of the main body part 19, the outer circumference has a regular octagonal shape. The mountain parts 23a and the valley parts 23b are provided from intermediate parts of respective facing sides of the regular octagon to the inner circumference. The shapes of the inner circumferences of the wave washers 23 are circular shapes in a manner similar to those in the Example 1.

Similar to the wave washers 23, in the linking members 21a and 21b, the outer circumference has a regular octagonal shape, and the inner circumference has a circular shape.

Figure 13:
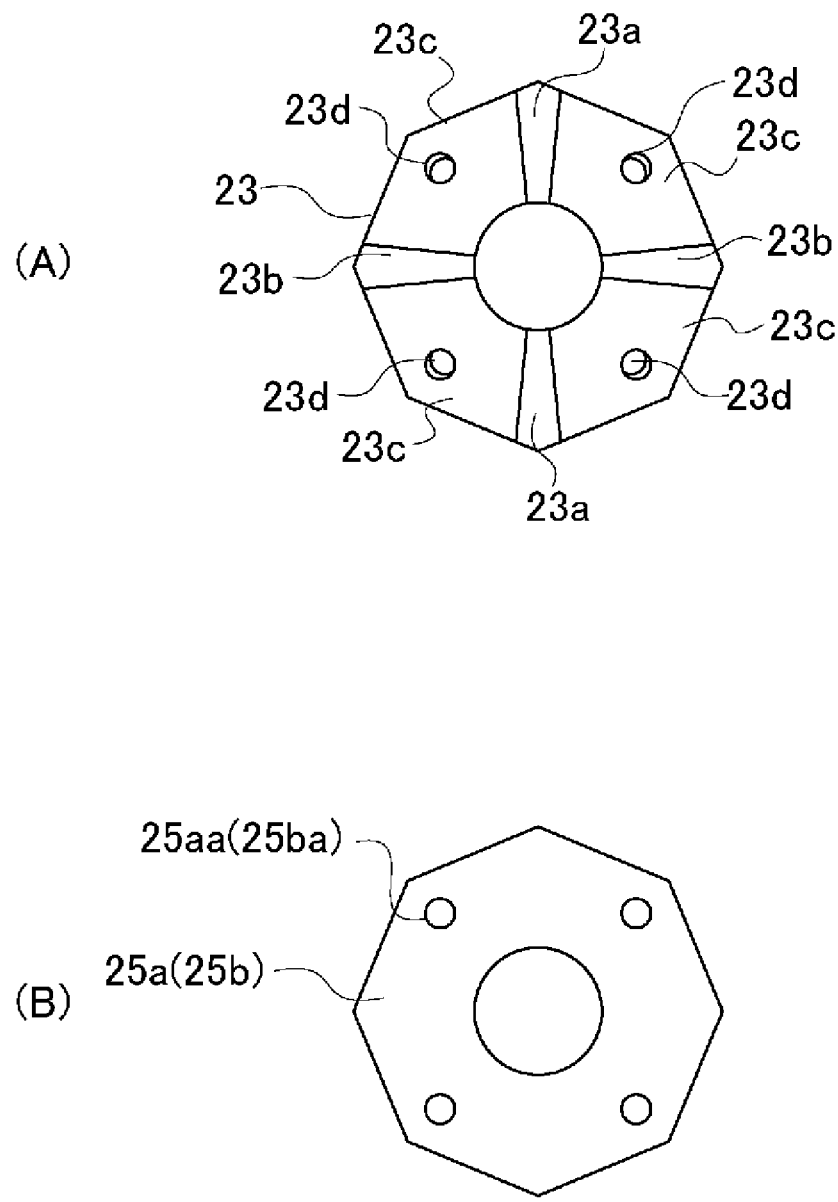
In FIG. 13, (A) is a plan view illustrating a wave washer used in a main body part of a flexible member according to a modification example of the Example 5, and (B) is a plan view illustrating a flat washer used in a linking part of the flexible member.

In FIGS. 13, (A) and (B) illustrate a modification example. (A) of FIG. 13 is a plan view illustrating the wave washer 23, and (B) of FIG. 13 is a plan view illustrating the flat washer 25a (25b).

In the modification example of FIG. 13, the outer circumference of each of the wave washers 23 of the main body part 19 has a regular octagonal shape, but the mountain parts 23a and the valley parts 23b are respectively provided from corners of a regular octagon to the inner circumference. The constitutions are otherwise the same as the constitutions of the Example 5 in (A) and (B) of FIG. 12.

In the present example and the modification example as well, it is possible to exhibit operational effects similar to those in the Example 1. In the present example and the modification example, the shapes of the outer circumferences of the wave washers 23 are changed compared to those in the Example 1, but the shapes of the inner circumferences may be changed compared to those in the Example 1.

The invention claimed is:

1. A flexible member comprising:
a main body part that has a plurality of wave washers stacked in an axial direction and joined to each other, and the main body part is able to be bent with respect to the axial direction due to elastic deformation of the wave washers; and
a linking member that is elastically deformable, the linking member being provided at an end of the main body part and being linked to another member,
wherein
a deformation amount of the linking member is smaller than a deformation amount of the wave washer, when the main body part is bent,
wherein the linking member is an annular plate member having the deformation amount smaller than the deformation amount of the wave washer of the main body part, wherein the plurality of wave washers individually includes a plurality of mountain parts and valley parts individually provided between the mountain parts in a circumferential direction, and adjacent wave washers abut each other, wherein the linking member comprises a plurality of flat washers stacked in the axial direction and directly joined to each other.

2. The flexible member according to claim 1, wherein the plurality of wave washers are joined in a state in which the mountain parts and the valley parts of adjacent wave washers abut each other, and wherein the plurality of flat washers is joined to each other at positions corresponding to joint portions of the wave washers.

3. The flexible member according to claim 1, wherein the linking member comprises: a plurality of flat washers stacked in the axial direction and joined to each other.

4. The flexible member according to claim 3, wherein the plurality of wave washers are joined in a state in which the mountain parts and the valley parts of adjacent wave washers abut each other, and wherein the plurality of flat washers is joined to each other at positions corresponding to joint portions of the wave washers.

* * * * *